US005115810A

United States Patent [19]

Watanabe et al.

[11] Patent Number: 5,115,810

[45] Date of Patent: May 26, 1992

[54] ULTRASONIC TRANSDUCER ARRAY

[75] Inventors: Kazuhiro Watanabe, Tokyo; Yasushi Hara, Kawasaki; Atsuo Iida, Yokohama; Takaki Shimura, Machida; Kiyoto Matsui; Hiroshi Ishikawa, both of Kawasaki; Kenji Kawabe, Yokohama, all of Japan

[73] Assignee: Fujitsu Limited, Kawasaki, Japan

[21] Appl. No.: 605,349

[22] Filed: Oct. 30, 1990

[30] Foreign Application Priority Data

Oct. 30, 1989 [JP] Japan ................................ 1-282254

[51] Int. Cl.[5] ................................................ A61B 8/14

[52] U.S. Cl. .............................. 128/662.03; 310/367; 310/334

[58] Field of Search .................... 128/662.03; 310/322, 310/334, 335, 336, 361, 367

[56] References Cited

U.S. PATENT DOCUMENTS

| | | | |
|---|---|---|---|
| 4,245,173 | 1/1981 | Zumsteg et al. | 310/361 |
| 4,348,609 | 9/1982 | Inoue | 310/367 |
| 4,385,255 | 5/1983 | Yamaguchi et al. | 128/662.03 |
| 4,398,325 | 8/1983 | Piaget et al. | 310/334 |
| 4,425,525 | 1/1984 | Smith et al. | 310/334 |
| 4,640,291 | 2/1987 | 't Hoen | 128/662.03 |

*Primary Examiner*—Francis Jaworski

*Assistant Examiner*—George Manuel

*Attorney, Agent, or Firm*—Staas & Halsey

[57] ABSTRACT

A plurality of rectangular piezo-electric ultrasonic sector transducers are aligned to form an array, and each transducer has first and second electrodes on its radiating surface. The first electrode is located on a center line of the sector transducer's length, and has a first length in the longitudinal direction and a first width along the center line. Two of the second electrodes are arranged outside the first electrode, symmetrical to the center line. The two second electrodes have a second length in the longitudinal direction longer than the first length, and have a second width which is almost the same as the first width, along a line near the center line. Thus, diamond-shaped electrodes excellent for providing a beam narrow in the longitudinal direction can be employed as the first electrode, and the combination of the first and second electrodes can be connected to each other. The first electrode is designed to provide an ultrasonic beam narrow at a distance shorter than a focal length of an acoustic lens provided on the transducers, and the combination of the first and second electrodes is used to provide an ultrasonic beam narrow in another distance substantially longer than the focal length, so that a sharp beam can be delivered for both the short distance and the long distance.

23 Claims, 9 Drawing Sheets

FIG. 13
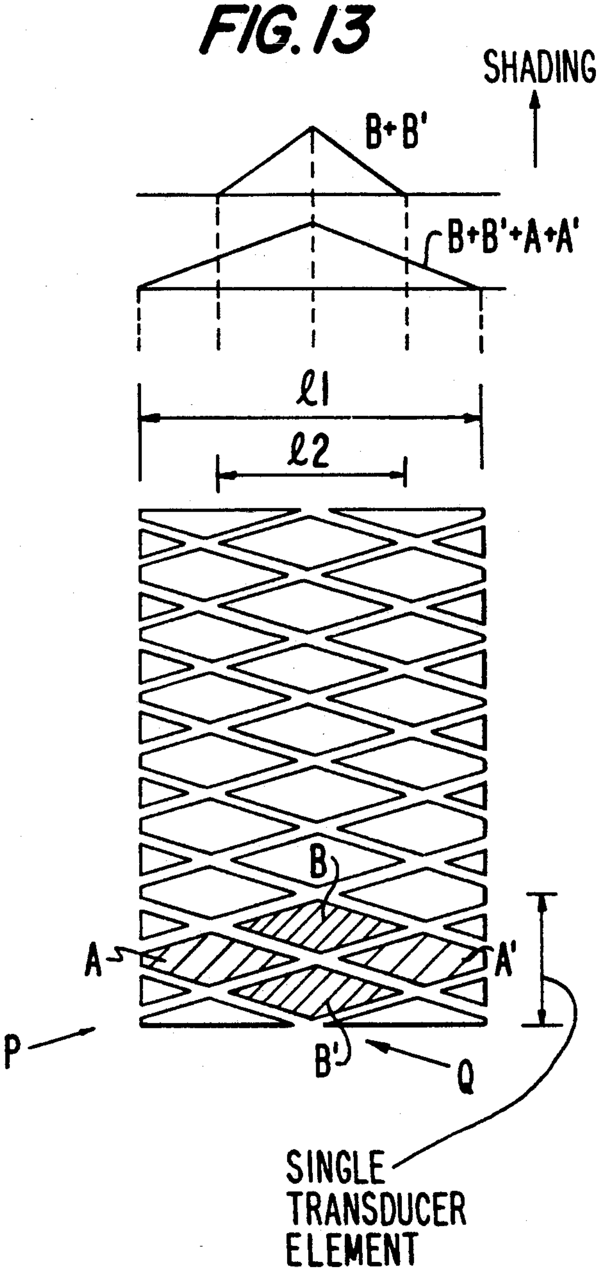
FIG. 14
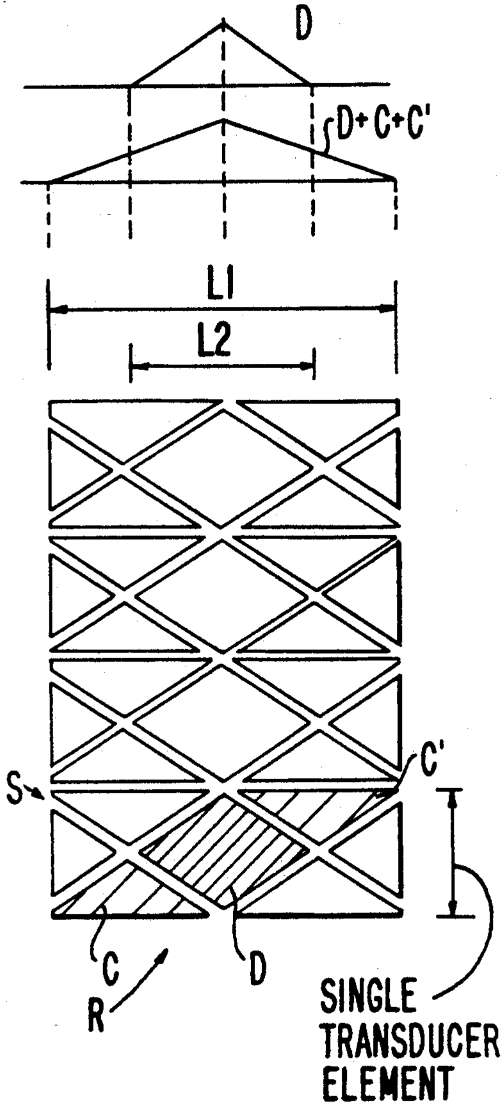
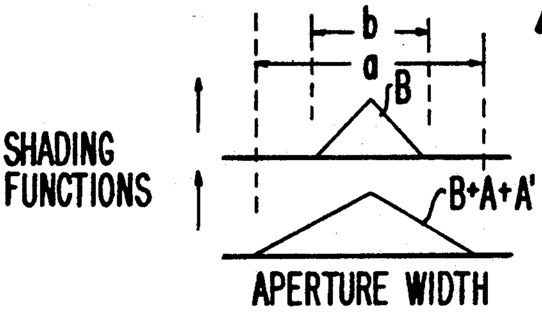
FIG. 11 (a)
FIG. 11 (b)

ULTRASONIC TRANSDUCER ARRAY

BACKGROUND OF THE INVENTION

1. Field of the Invention

The present invention relates to an improvement in an ultrasonic transducer, namely an ultrasonic probe to realize a high resolution ultrasonic diagnostic equipment by sharpening ultrasonic beam width in the direction of elevation orthogonally crossing the azimuth plane (i.e., the direction of Y axis).

2. Description of the Related Art

An ultrasonic transducer array, i.e. an ultrasonic probe arranging a plurality of rectangular transducer elements (hereinafter referred to as transducer elements) is widely used as a probe for electronically scanning an ultrasonic beam. In such an ultrasonic probe, a narrow beam has been required for near field to far field in order to realize such high resolution ultrasonic diagnostic equipment. Improvement of the resolution characteristic in the array direction (i.e. azimuth direction) has been conducted by electronic control of phase or amplitude of the transmitting or receiving wave of each transducer element, while that in the Y axis direction has been conducted by an acoustic lens. However, the beam width in the Y axis direction has a problem in that the beam becomes wide in fields other than the vicinity of the focal point of the acoustic lens.

Therefore, the following method has been employed in order to improve the beam characteristic in the Y axis direction from near field to far field.

FIG. 1(*a*) is a perspective view of an ordinary ultrasonic transducer array, i.e. an ultrasonic probe arranging a plurality of rectangular transducer elements 1. These rectangular elements are formed by dicing the piezo-electric ceramic plate having electrodes on its two surfaces, along the Y direction. The electrode on one of the surfaces is led out to the apparatus body by a flexible print card FPC 4 as a ground electrode, while the electrode on the other surface is led out as a signal electrode. The surface radiating the ultrasonic power (towards the upper side in FIG. 1(*a*) is generally the ground electrode; however, signal electrodes, which should not actually be seen, are drawn on the side of the radiation surface throughout the drawings for convenience of explanation.

FIG. 1(*b*) shows the signal electrode pattern, namely, the aperture shape of each transducer element 1 and its shading function which indicates the weight of radiation power. The weight is substantially proportional to electrode width in the X direction. Therefore, in the case of the rectangular electrode of FIG. 1(*b*) where the shading function is flat, no weighting is conducted. The azimuth plane is a plane in which ultrasonic beam scans in the axial direction (Z direction) perpendicular to the surface of transducer array, as shown in FIG. 1(*a*). An acoustic lens 3 is provided to narrow the ultrasonic beam width in the Y axis direction. The ultrasonic beam width, when the focal distance is 140 mm, is shown in FIG. 2, where beam widths of the beams radiated from a probe 20 mm wide in the Y direction are −10 dB and −20 dB lower than the center value as shown by curves (A) and (B), respectively. As is apparent from this figure, a narrow beam can be obtained in the vicinity of the focal distance 140 mm of the lens; however, the beam width becomes wider in the nearer or farther field than the focal distance of lens.

As a method of improving the ultrasonic beam characteristic, a probe which is structured so that the Y direction width of the transducer element, namely the aperture, is selected depending on the diagnostic distance, is shown in FIG. 3, where the signal electrodes of the transducer element are divided into A, B and A'. The central signal electrode B is selected for diagnosis of near field, i.e. at a distance shorter than the focal distance, and signal electrodes A, B and A' are used for diagnosis of far field, i.e. at a distance longer than the focal distance. This method accomplishes ultrasonic beam characteristics in which the −10 dB beam width (A) is improved around the focal distance; however, the −20 dB beam width (B) is not improved yet (see FIG. 4). FIG. 5 shows a third prior art arrangement such as disclosed in U.S. Pat. No. 4,425,525, in which the beam width is further narrowed by weighting the radiation power along the Y direction. In this case, the radiation power is weighted by varying the signal electrode width (diamond shape in FIG. 5) in the longitudinal direction (Y direction) of each transducer element, as shown in the shading function of FIG. 5. As a result, as shown in FIG. 6, the −20 dB beam width (B) before and after the focal point of the lens, is improved; however, the improvement of the −10 dB beam width (A) in the near field before the focal point is still insufficient.

FIG. 7 is a diagram for illustrating a fourth prior art method combining the method of FIG. 3 and the method of FIG. 5. As shown in FIG. 8, the −10 dB width (A) in the near field before the focal point is improved; however, there is a problem left unsolved in that the improvement of the −20 dB beam width (B) is still small, since the weighting is insufficient when only the signal electrode B is selected.

SUMMARY OF THE INVENTION

It is therefore an object of the present invention to provide a high-resolution ultrasonic diagnostic apparatus and an ultrasonic probe employed therein which accomplishes a narrow ultrasonic beam particularly in a direction orthogonal to its scan plane, for both near and far field of the diagnosis.

A plurality of rectangular piezo-electric ultrasonic transducer elements are laterally aligned to form an array, where each transducer element has first and second signal electrodes on one of its surfaces. The first signal electrode is located on the center of the transducer element, so as to have a first length in the longitudinal direction and a first width along its lateral center line. Two of the second signal electrodes are arranged outside the first electrode, symmetrically to the lateral center line.

The two second signal electrodes have a second length in the longitudinal direction longer than the first length, and have a second width almost the same as the first width, along the lateral center line. Thus, diamond-shaped electrodes excellent for providing an ultrasonic beam narrow in the electrode's longitudinal direction can be realized within the first signal electrode and by the combination of the first and second signal electrodes connected all together. Diamond-shaped signal electrodes radiate ultrasonic power more weighted at the central portion than at their longitudinal end portions. The first signal electrode is used to transmit an ultrasonic beam narrow at a distance shorter than a focal length of an acoustic lens provided on the transducer's surface, and the combination of the first and secons signal electrodes are used to transmit an ultrasonic beam narrow at another distance longer than the focal length, so that a sharp beam can be accomplished for both the short distance and long distance of the ultrasonic diagnosis.

The above-mentioned features and advantages of the present invention, together with other objects and advantages, which will become apparent, will be more fully described hereinafter, with reference being made to the accompanying drawings which form a part thereof, wherein like numerals refer to like parts throughout.

BRIEF DESCRIPTION OF THE DRAWINGS

FIG. 1(*b*) is a diagram of the transducer elements employed in FIG. 1(*a*);

FIG. 11(*a*) is a diagram of the shading function of the FIG. 10 transducer elements employing signal electrode B;

FIG. 11(*b*) is a diagram of the shading function of the FIG. 10 transducer elements employing signal electrodes B+A+A';

FIG. 13 is a diagram of the second preferred embodiment of the present invention and the shading functions thereof;

FIG. 14 is a diagram of a third preferred embodiment of the present invention and the shading functions thereof;

DESCRIPTION OF THE PREFERRED EMBODIMENTS

Preferred embodiments of the present invention will be explained in detail with reference to the accompanying drawings.

Figure 9:
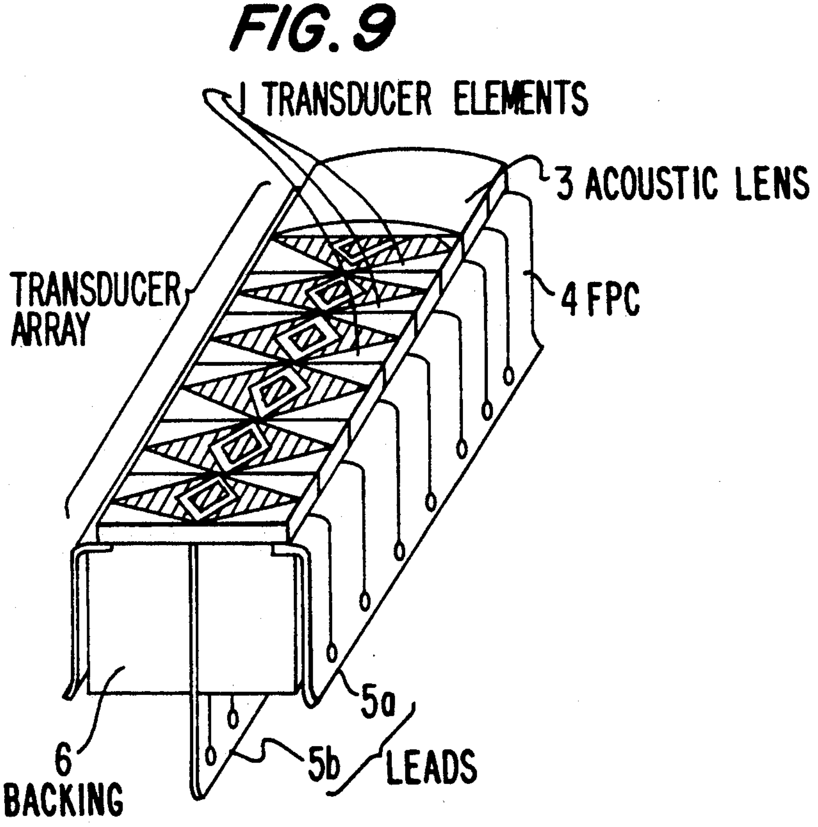
FIG. 9 schematically illustrates an array type ultrasonic probe according to the present invention, where the lower electrodes which should not be seen are drawn on the upper surface.

FIG. 9 is a perspective view of a transducer array, namely a probe of a first preferred embodiment of the present invention.

Figure 10:
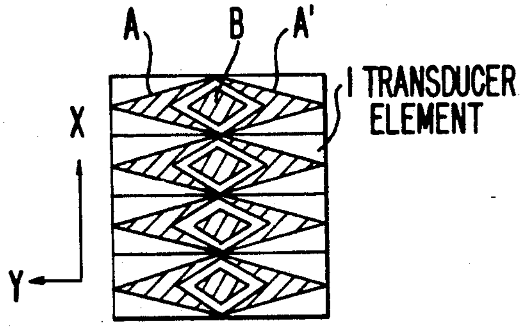
FIG. 10 is a plan view of the transducer elements employed in the FIG. 9 array.
Figure 8:
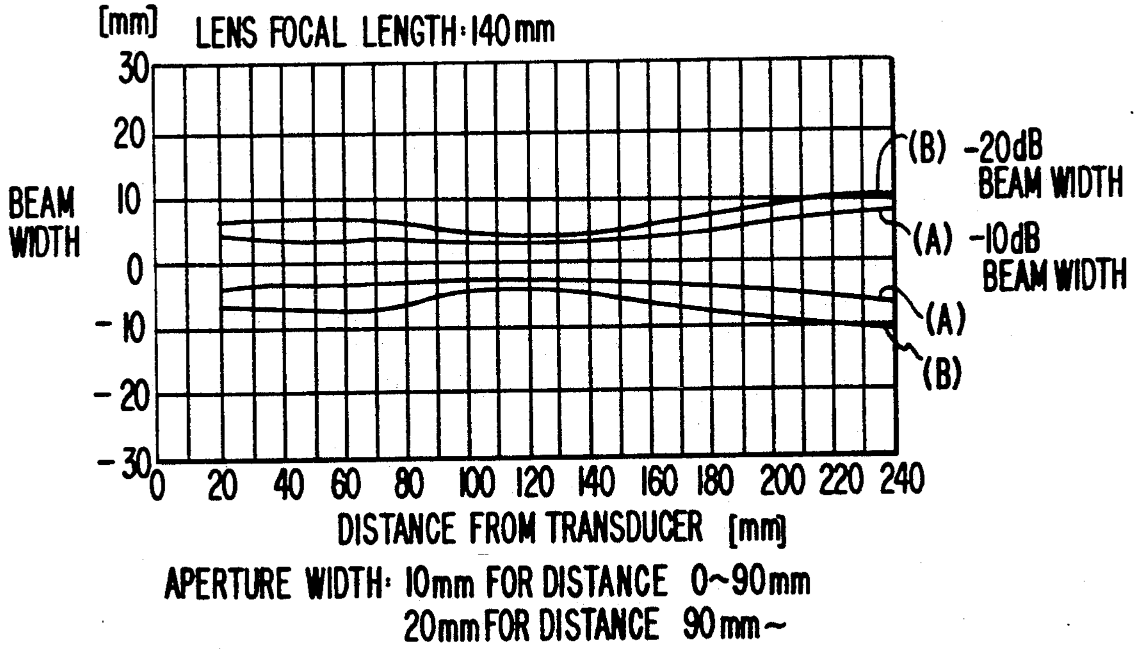
FIG. 8 PRIOR ART
FIG. 8 is a graph of beam width characteristics of the FIG. 7 prior art transducer elements.

FIG. 10 is a plan view of signal electrodes of the probe of the first preferred embodiment. FIG. 11(*a*) and 11(*b*) are graphs of shading functions indicating the weighting in the Y direction.

Figure 12:
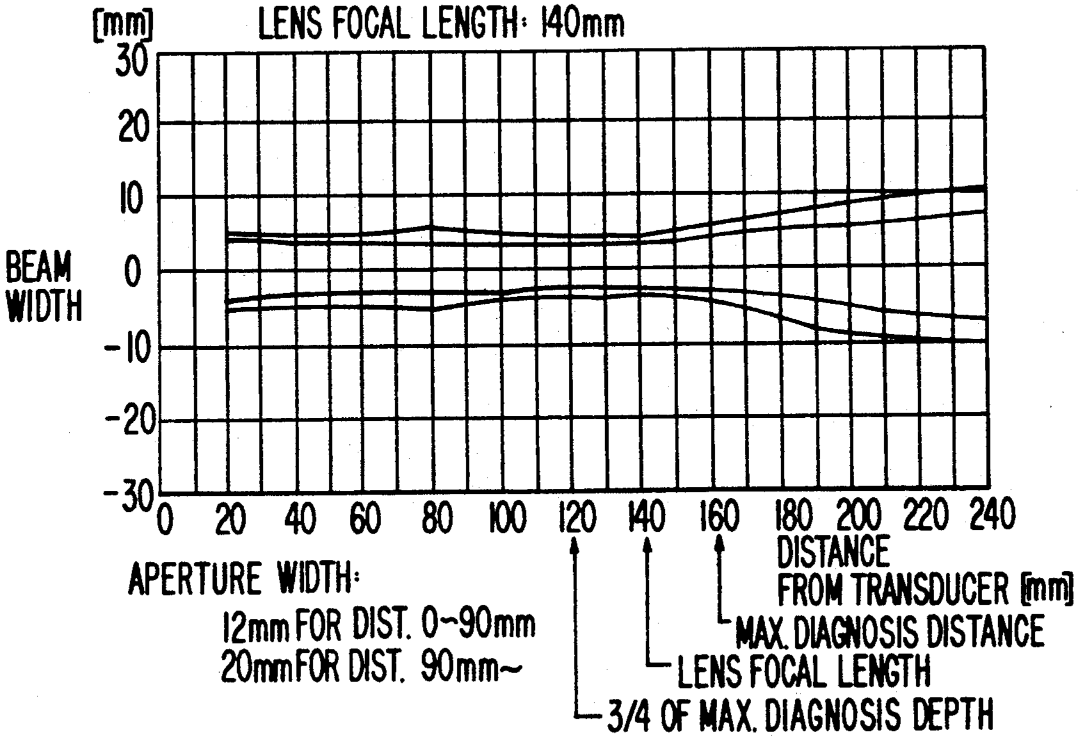
FIG. 12 is a graph of the beam width characteristics of the FIG. 10 transducer elements.

FIG. 12 is a graph of an ultrasonic beam width characteristic of the first preferred embodiment of the present invention.

Each transducer element 1 is formed with generally employed lead zirconate titanate crystal $Pb(Ti,Zr)O_3$ (generally referred to as PZT) ceramic, for example, of 0.6 mm in width, 20 mm in length and about 0.45 mm in thickness. In the direction thereof, 100 to 200 transducer elements 1 are arranged to form an array. Metal films are deposited on two surfaces of transducer element 1, usually by evaporation, so as to form electrodes. The film electrode on one of the surfaces of the transducer element 1 is divided to form the shape of diamond typically by the etching method, as shown in FIG. 10, so that the signal electrodes A, B and A' are formed. Longitudinal (Y direction) ends of the first signal electrodes A and A' extend to reach the longitudinal length "a" of each transducer element. The longitudinal length of the second signal electrode B is, for example, 10 to 20 mm. These signal electrodes are insulated by the gap of about 20 μm from each adjacent signal electrode. The first signal electrodes A and A' are led out by a lead wire 5*a* provided on a flexible print card 4 (hereinafter referred to as FPC) and are connected with each other on the FPC 4. The second signal electrode B is also led out by a lead wire 5*b* on FPC 4. Lead wire 5*a* is connected or disconnected, in accordance with a predetermined sequence, to or from lead wire 5*b* by a driving circuit which will be described below. When leads 5*a* and 5*b* are connected to each other, the first and second signal electrodes A, B and A' are driven simultaneously so as to have a sufficiently weighted aperture of width "a" having a triangle shading function B+A+A' shown in FIG. 11(*b*). When they are disconnected, only the second signal electrode B is driven and the ultrasonic power is radiated from the aperture of width "b" sufficiently weighted by a triangle shading function B shown in FIG. 11(*a*). The film electrode formed on the other surface of transducer element 1, namely on the front side surface, is grounded as a common electrode. A backing 6 (FIG. 9) made of a material which well absorbs ultrasonic beams, attenuates ultrasonic radiation towards the rear side.

With the above transducer array configuration, the maximum diagnostic distance is about 160 mm when it is applied to diagnosis of the human body. Therefore, there is provided on the radiation surface of the transducer array an acoustic lens 3, which works as a convex lens for the an ultrasonic wave of 3.5 MHz, which is the resonance frequency of the 0.45 mm thick transducer element, formed with a silicone resin having a cylindrical surface to have approximately 140 mm focal distance. The second signal electrode B having the shorter aperture width "b" is effective for reducing the beam width in the range from the focal distance of the acoustic lens 3 to the about 90 mm distant field, which is nearer than the focal distance of the lens. The parallel connection of all the signal electrodes A, A' and B having the wider aperture "a" in the Y direction, is effective for reducing the beam width at the approximately 150 mm distant field, and accordingly contributes to the improvement of the characteristic in the far field farther than the focal distance of acoustic lens 3. In the above description, the transducer is explained to be used for transmitting an ultrasonic wave; however, as is well known, the same ultrasonic transducer is used for receiving an ultrasonic wave.

Figure 17:
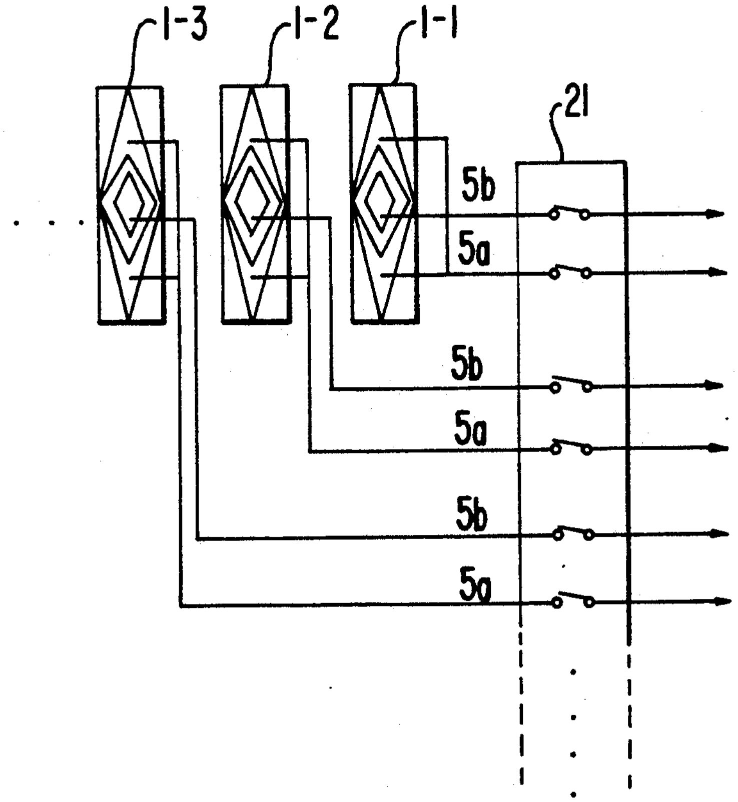
FIG. 17 is a bock diagram of an ultrasonic diagnostic equipment employing the FIG. 9 ultrasonic transducers of the present invention.

A circuit configuration of ultrasonic diagnostic equipment employing the above-explained transducer array is shown in FIG. 17. Lead wires 5a and 5b of the first signal electrodes A and A' and the second signal electrode B of the transducer elements 1-1, 1-2, . . . are connected directly or via amplifier transistor to the terminal of switches 21. The opposite terminals of switches 21 are selectively connected to a transducer driving circuit (a pulser) or a receiver circuit to receive an ultrasonic signal reflected from an object in the human body to diagnose (hereinafter referred to as echo) according to a predetermined sequence. An output of the receiver input to a display unit so as to be displayed thereon. The sequence of the switching is basically as follows:

1. A driving pulse is applied via lead 5b to the second signal electrode B of the first transducer element 1-1 for the near field diagnosis.
2. An echo is received while the electrode is kept connected.
3. A driving pulse is applied via leads 5a and 5b to the first and second signal electrodes A, B and A' connected in parallel of the first transducer element 1-1 for the far field diagnosis.
4. An echo is received while the electrodes are kept connected. However, during the reception of the echo from the near field to be conducted by the first signal electrode alone in the third and fourth sequences, reception of the echo or input to the display unit is disabled.
5. The above sequences are carried out for adjacent transducer elements 1-2, 1-3, . . . , so that scanning is carried out.

Though in the above sequence the scanning is carried out of the adjacent transducer element, some of the neighboring elements may be selected at the same time according to the design requirement of the system.

The thus formed ultransonic beam characteristic is shown in FIG. 12. As seen in this figure, the improvement of the −20 dB beam width (B) is distinctive in comparison with the prior arts in achieving a narrow ultrasonic beam for all the fields (distances).

As a variation of the first preferred embodiment, the following signal electrode configurations may be alternatively employed:

(1) Though in the above preferred embodiment diamond electrodes are employed which are symmetrical for X and Y axes, they may be asymmetrical to a certain degree for the convenience of manufacturing or other reasons. In this case, the shape of the radiation beam causes No problem in practical use.

Figure 1:
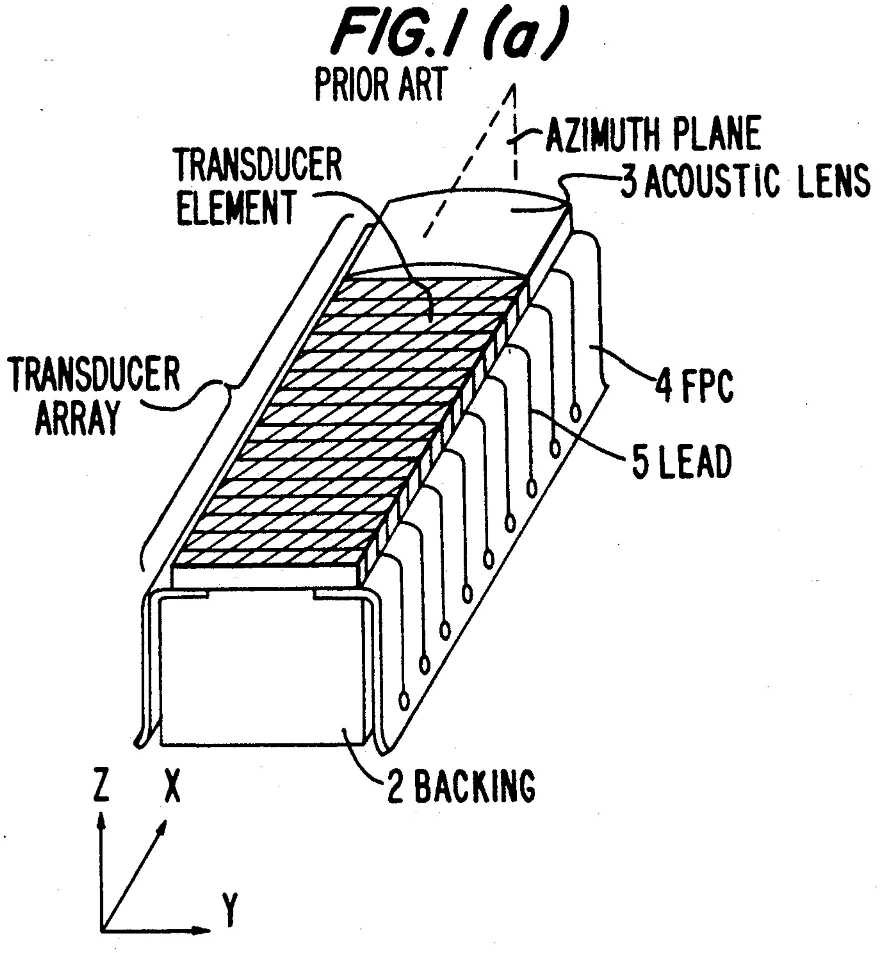
FIG. 1 (a) PRIOR ART
FIG. 1(*a*) is a schematic diagram which illustrates an array type prior art ultrasonic probe, where the lower electrodes which should not be seen are drawn on the upper surface.
Figure 1:
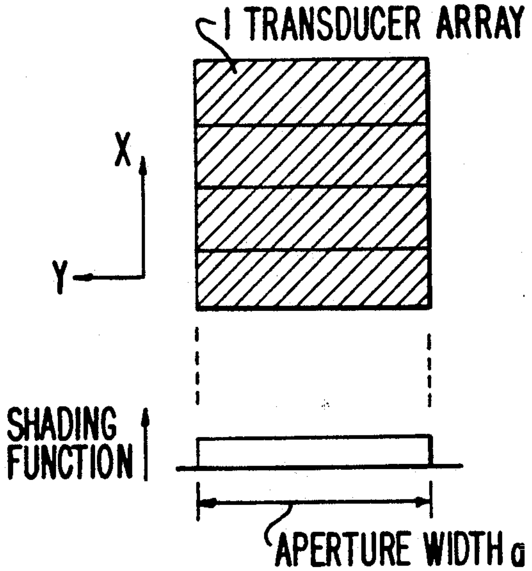
FIG. 1 (b) PRIOR ART
Figure 2:
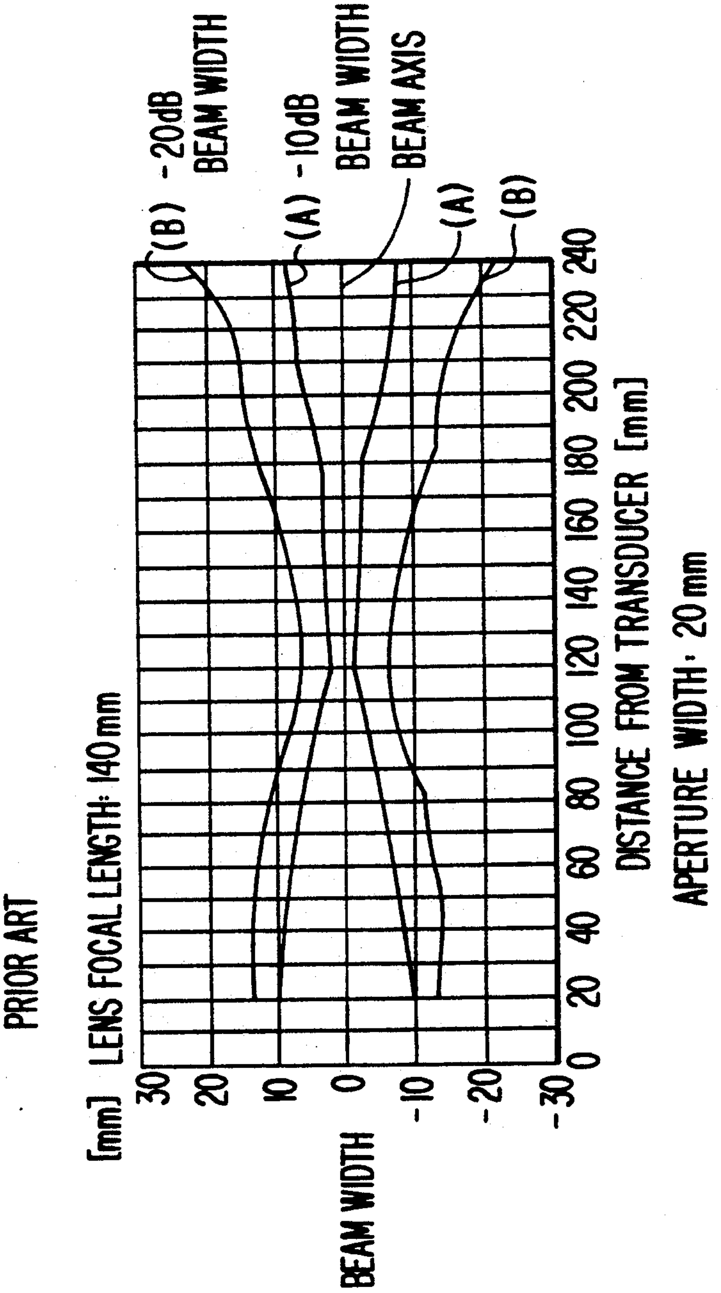
FIG.2 PRIOR ART
FIG. 2 is a graph of the beam width characteristics of the prior art probe of FIGS. 1(*a*) and 1(*b*)
Figure 3:
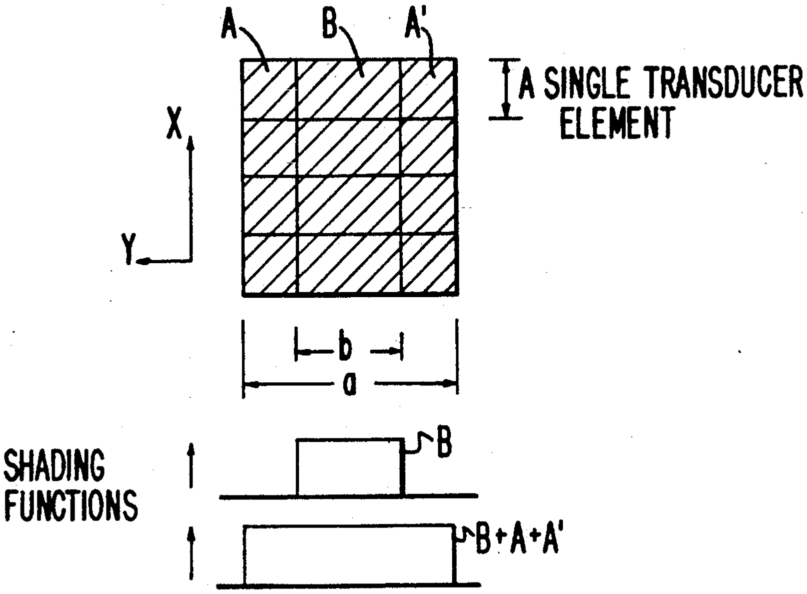
FIG. 3 PRIOR ART
FIG. 3 is a diagram of second prior art ultrasonic transducer elements.
Figure 4:
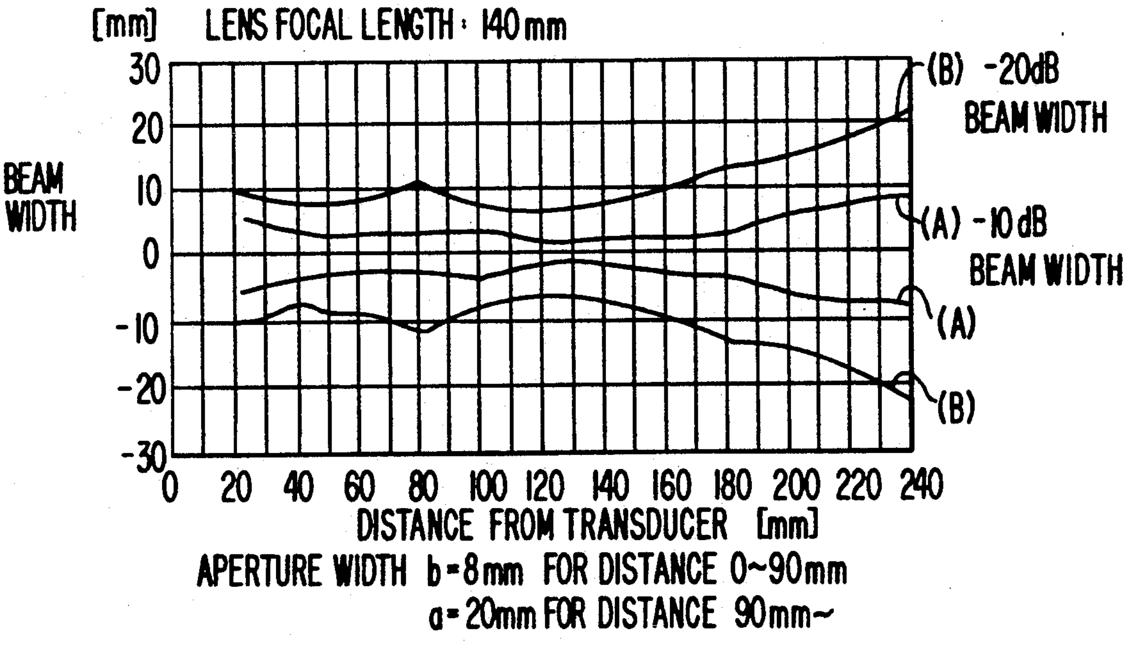
FIG. 4 PRIOR ART
FIG. 4 is a graph of the beam width characteristics of the FIG. 3 prior art transducer elements.
Figure 5:
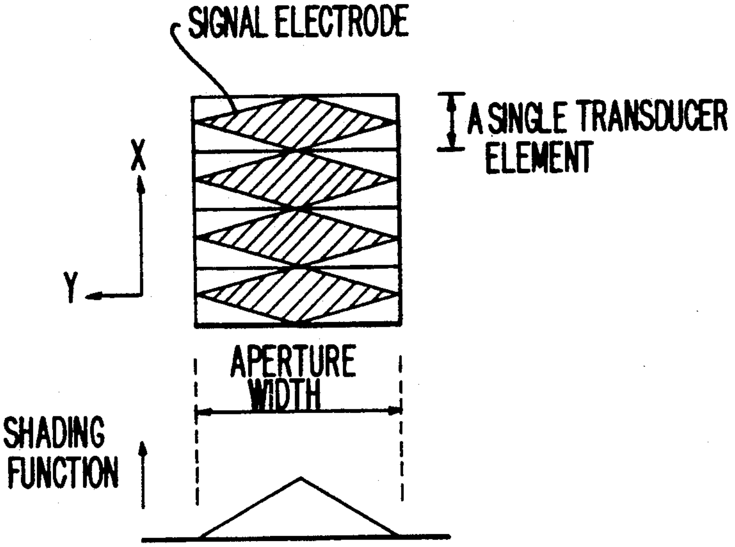
FIG. 5 PRIOR ART
FIG. 5 is a diagram of third prior art ultrasonic transducer elements.
Figure 6:
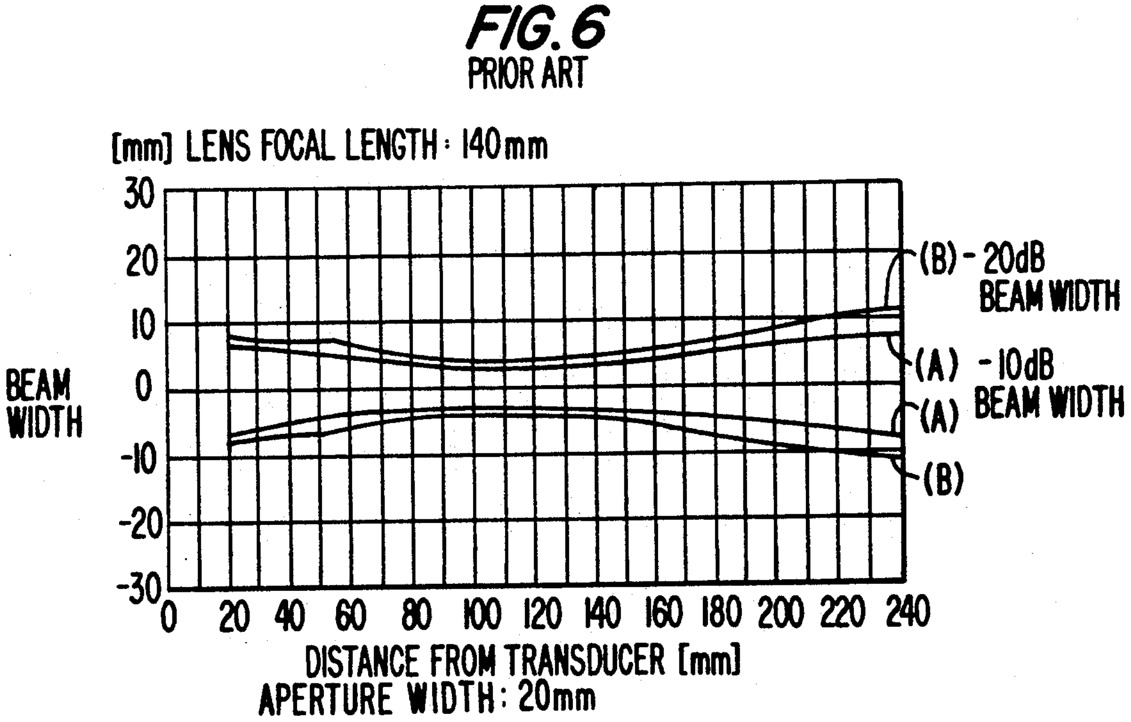
FIG. 6 PRIOR ART
FIG. 6 is a graph of the beam width characteristics of the FIG. 5 prior art transducer elements.
Figure 7:
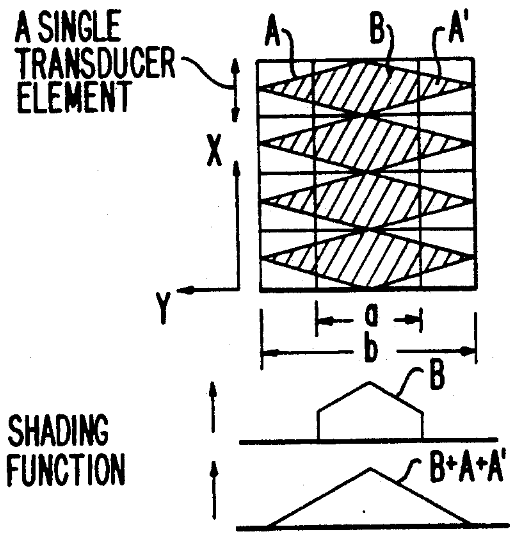
FIG. 7 PRIOR ART
FIG. 7 is a diagram of fourth prior art ultrasonic transducer elements.

(2) Though in the above preferred embodiments the outlines of the electrodes are shown as substantially of diamond shapes, in other words, the widths at the longitudinal ends of the electrodes are sharp, it is apparent the longitudinal ends may have some width like the electrode "B" of FIG. 7. The longitudinal end widths of the first and/or second electrode(s) are generally chosen to be below 0.5, preferably below 0.3, of the widths at the central portion of the electrodes. The ends widths are determined as a compromise between the required weighting and problems encountered in the design and production.

(3) The ground electrode explained above may be either a common film electrode continuous upon all the transducer elements, or may be of the same shape as the signal electrodes explained above, where the same effect can also be obtained.

(4) Each of the diamond ridges is required just to be narrowing toward the ends from the central area, accordingly, may be a curve. Thereby, the shading function can be freely adjusted.

(5) As the diamond signal electrode B exists coaxially in double in the signal electrodes A and A', another signal electrode may be additionally provided within signal electrode B. Namely, signal electrodes may be provided coaxially in triplicate so as to be selected for their suitable distances.

Figure 15:
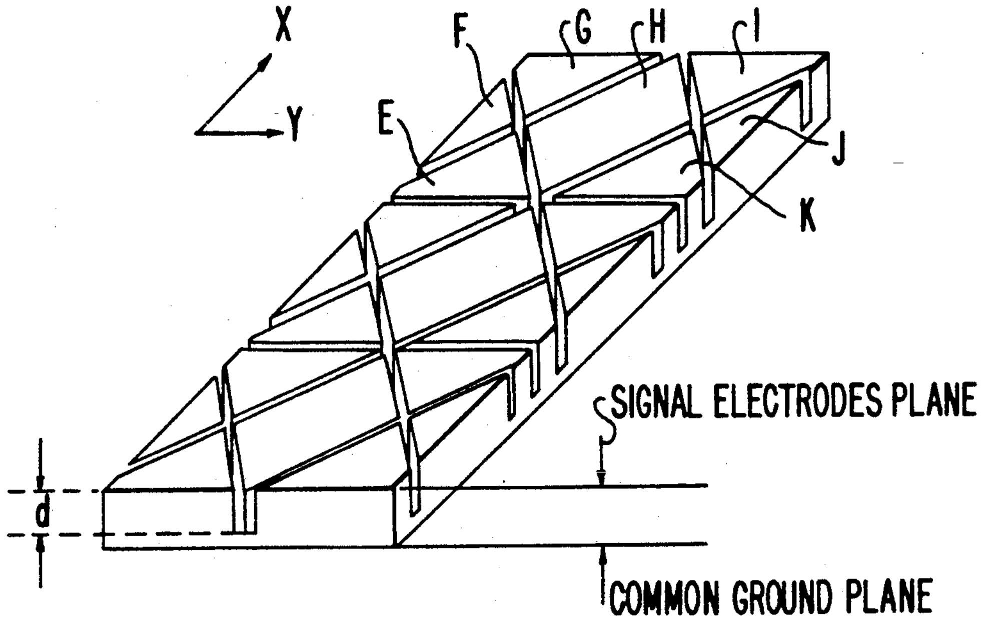
FIG. 15 is a diagram for describing a dicing method employed in the FIG. 13 and FIG. 14 preferred embodiments.

FIG. 13 shows the configuration and its shading function of a transducer of a second preferred embodiment in accordance with the present invention. FIG. 15 is a perspective view for explaining a dividing method used in the second preferred embodiment and in a third preferred embodiment to be explained below. A piezoelectric material plate having electrodes on its two surfaces is divided by dicing along two directions P and Q (see FIG. 13), each obliquely crossing the X axis and mutually-crossing symmetrically for the X axis, each in parallel by the pitch of two lines per single transducer element, so that a plurality of divided elements are formed. For the 0.45 mm thick piezo-electric material plate, its groove width by the dicing is about 0.05 mm, and its depth d is about 0.4 mm. In FIG. 13, the four divided elements A, A', B and B' constitute a single transducer element which corresponds to single transducer element 1 of FIG. 10. Divided elements B and B' having the short aperture $l_2$ are selected for near field diagnosis, and all the divided elements, A, A', B and B', having the wider aperture $l_1$ are selected for far field diagnosis. Thereby, the respective aperture sizes $l_1$ and $l_2$ can provide the weighting in the Y axis direction similar to that in the first preferred embodiment, as shown with the shading functions in FIG. 13.

FIG. 14 shows a configuration and its shading functions of a third embodiment of the present invention. In addition to the diced grooves R and S obliquely crossing each other with the pitch of single line per single transducer element, grooves in the Y direction are additionally provided so as to separate the transducer elements. An L1 wide aperture is obtained by selecting the divided elements C, D and C', while and L2 wide aperture is obtained by selecting the divided element D. Thereby, sufficient weighting in the Y direction can be realized as shown with the shading functions in FIG. 14.

In the above second and third preferred embodiments, the divided elements, for example, E to K in FIG. 15, are connected with each other at their bottom side; however, it is apparent that they may be separated perfectly. Or, as explained in the first preferred embodiment, the signal electrodes may be patterned by etching the electrodes. It is impossible to form the pattern shown in FIG. 10 by dicing. However, the electrode patterns of FIGS. 13, 14 and 15 can be formed by dicing. Divided elements by the dicing method causes less acoustic coupling between adjacent divided elements so as to reduce undesirable radiation from the adjacent divided element.

As described above, FIG. 12 shows the ultrasonic beam width characteristic of the transducer elements described in the first embodiment, namely the configuration where the focal distance of acoustic lens 3 is set to 140 mm which is longer than $\frac{3}{4}$, i.e. 120 mm, of the maximum diagnosis depth 160 mm of ultrasonic diagnostic equipment.

Figure 16:
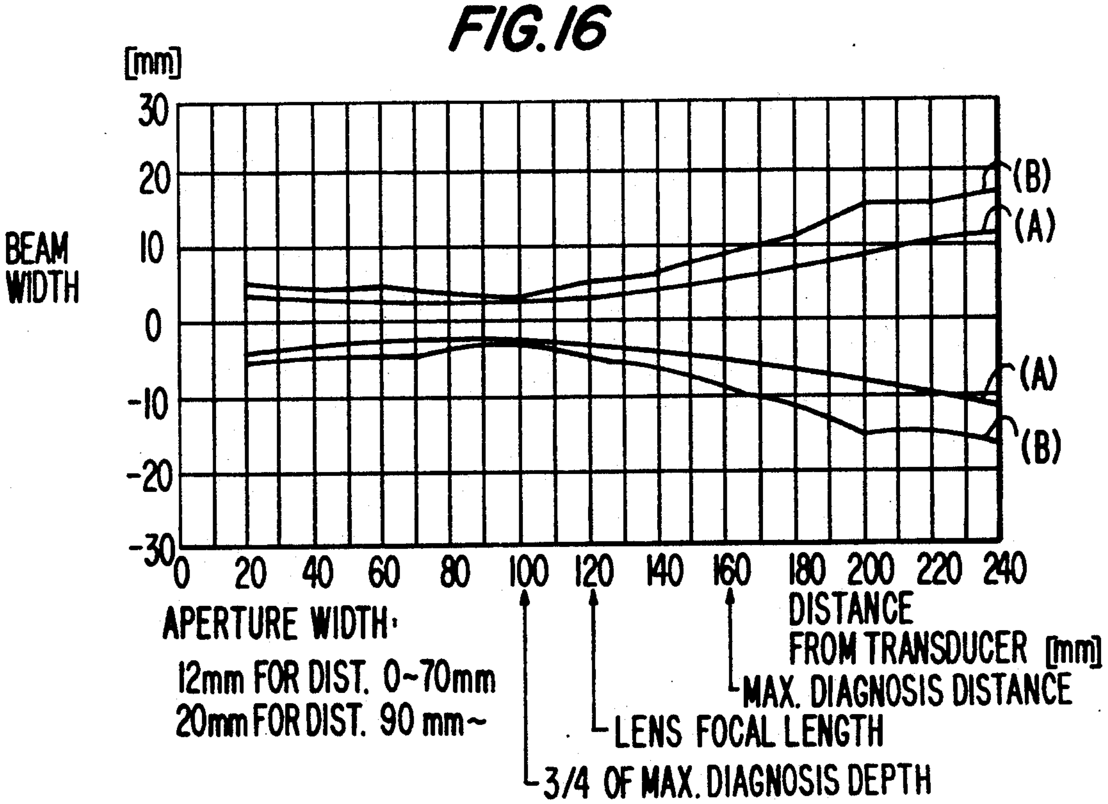
FIG. 16 is a graph of the beam width characteristics of the FIG. 10 transducer elements specifically employing an acoustic lens having focal length shorter than three quarters of maximum diagnostic depth of the transducer.

FIG. 16 shows the ultrasonic beam width characteristic for the focal distance set to 100 mm which is shorter than $\frac{3}{4}$ of the maximum diagnostic depth. In FIG. 16, it is seen that the ultrasonic beam spreads at the deep diagnostic zone. However, in FIG. 12, a uniform and narrow ultrasonic beam can be accomplished in the entire diagnostic zone. As explained above the maximum diagnostic depth of the probe having the resonance frequency of 3.5 MHz is about 160 mm; and the maximum diagnostic depth of about 0.32 mm thick probe having the resonance frequency of 5.0 MHz is about 110 mm. Therefore, the focal distance of acoustic lens 3 should be desirably set to 120 mm or longer, and 80 mm or longer, respectively, which are $\frac{3}{4}$ of the respective maximum diagnostic depths, so as to obtain high resolution in both near and far fields.

Thus, the present invention provides a probe having a plurality of aperture types, so that sufficient weighting is accomplished for respective types of apertures. The ultrasonic beam width in its short axis direction of the probe being reduced for both the near and far field diagnosis contributes to an accomplishment of a high resolution ultrasonic diagnostic equipment.

Though the preferred embodiments described above employ an array of a plurality of transducer elements, it is apparent that the present invention can be applied to a single transducer element.

Moreover, though in the above preferred embodiments an acoustic lens is provided at the radiation surface of transducer array, it is also apparent that the structure of the transducer element according to the present invention can also be applied to the case where no acoustic lens is used.

The preferred embodiments described above can be used not only in the diagnostic of the human body but also can naturally be applied to an ultrasonic radar apparatus to detect other objects, for example, to an ultrasonic flaw detector, etc.

The many features and advantages of the invention are apparent from the detailed specification and thus, it is intended by the appended claims to cover all such features and advantages of the methods which fall within the true spirit and scope of the invention. Further, since numerous modifications and changes will readily occur to those skilled in the art, it is not desired to limit the invention and accordingly, all suitable modifications and equivalents may be resorted to, falling within the scope of the invention.

What I claim is:

1. A piezo-electric ultrasonic transducer long in a Y direction and short in an X direction which is substantially orthogonal to the Y direction, said transducer having major surfaces substantially parallel to the X and Y directions, said transducer radiating ultrasonic power in a Z direction which is substantially orthogonal to the X and Y directions, the transducer comprising:

a plurality of electrodes on one of the major surfaces, said electrodes comprising:

at least one first electrode located on a center line along the Y direction length of said transducer, said first electrode having a first length in the Y direction, said first electrode having a first width in the X direction at a central portion of the first length and having a second width at the Y direction ends thereof, the first width being greater than the second width; and at least two second electrodes arranged respectively on both sides of the center line, outlines of said two second electrodes having outlines with a second length in the Y direction which is substantially greater than the first length, the outlines of said second electrodes having a third width at the central portion of the second length and having a fourth width at the Y direction ends thereof, the third width being greater than the fourth width, said first electrode selectively providing an ultrasonic beam narrow in the Y direction at a first distance from said transducer, and said second electrodes being selectively connected to said first electrode so as to provide an ultrasonic beam narrow in the Y direction at a second distance substantially longer than the first distance.

2. An ultrasonic transducer as recited in claim 1, wherein the width of said first electrode gradually decreases from the first width to the second width.

3. An ultrasonic transducer as recited in claim 1, wherein the width of the outlines of said second electrodes gradually decreases from the third width to the fourth width.

4. An ultrasonic transducer recited in claim 1, wherein said first electrode and said second electrodes are symmetric with respect to one of the center line and a mid point of said transducer.

5. An ultrasonic transducer as recited in claim 1, wherein said first electrode is substantially diamond shaped.

6. An ultrasonic transducer as recited in claim 1, wherein the outlines of said second electrodes are substantially diamond shaped.

7. An ultrasonic transducer as recited in claim 1, wherein the second width is less than substantially 0.5 of the first width.

8. An ultrasonic transducer as recited in claim 7, wherein the second width is less than substantially 0.3 of the first width.

9. An ultrasonic transducer as recited in claim 1, wherein the fourth width is less than substantially 0.5 of the third width.

10. An ultrasonic transducer as recited in claim 9, wherein the fourth width is less than substantially 0.3 of the third width.

11. An ultrasonic transducer as recited in claim 1, wherein a ratio of a decrease from the first width to the second width is substantially equal to a ratio of a decrease from the third width to the fourth width.

12. An ultrasonic transducer as recited in claim 1, wherein said transducer further comprises an acoustic lens positioned for focusing an ultrasonic beam radiated therefrom, wherein said acoustic lens has a focal length for the ultrasonic beam.

13. An ultrasonic transducer as recited in claim 12, wherein the focal length is chosen to be longer than substantially three quarters of a maximum detectable distance of said transducer.

14. An ultrasonic transducer as recited in claim 12, wherein the focal length is substantially longer than the first distance and substantially shorter than the second distance.

15. An ultrasonic transducer as recited in claim 1, wherein a plurality of said transducers are aligned in the X direction so as to form a transducer array.

16. An ultrasonic transducer as recited in claim 1, further comprising a grounding electrode on another one of the major surfaces.

17. An ultrasonic detection apparatus comprising:

a plurality of piezo-electric ultrasonic transducer elements long in a Y direction and short in an X direction which is orthogonal to the Y direction, each of said transducer elements having major surfaces parallel to the X and Y directions, each of said transducer elements radiating ultrasonic power in a Z direction which is substantially orthogonal to the X and Y directions, each of said transducer elements comprising:

a plurality of electrodes on one of the major surfaces, said electrodes comprising:

at least one first electrode located on a center line along the Y direction length of said transducer, said first electrode having a first length in the longitudinal Y direction, said first electrode having a first width in the X direction at a central portion of said first length and having a second width at longitudinal ends thereof, the first width being greater than the second width; and at least two second electrodes arranged respectively on both sides of the center line, outlines of said at least two second electrodes having a second length in the Y direction which is substantially longer than the first length, the outlines of said second electrodes having a third width at the central portion of the second length and having a fourth width at Y direction ends thereof, the third width being wider than the fourth width, said first electrode selectively providing an ultrasonic beam narrow in the Y direction at a first distance from said transducer, and said second electrodes being selectively connected to said first electrode so as to provide an ultrasonic beam narrow in the Y direction at a second distance which is substantially greater than said first distance, said apparatus further comprising:

an electronic circuit connected to said transducer, for applying a first pulse signal to said first electrode of one of said transducers, for receiving a first echo signal of the first pulse signal, for applying a second pulse signal to said second electrode of the connected transducer, and for receiving a second echo signal of the second pulse signal; and display means for displaying the first and second echo signals, whereby said first electrode detects an object at a first distance from said transducer, and said second electrodes detect an object at a second distance which is substantially greater than said first distance.

18. An ultrasonic transducer as recited in claim 17, wherein a plurality of said transducer elements are aligned in the X direction so as to form a transducer array, and wherein after said electronic circuit completes the sequence for one of said transducers said electronic circuit is switched to a transducer adjacent thereto so as to repeat the sequence.

19. An ultrasonic transducer as recited in claim 18, wherein said array further comprises an acoustic lens positioned for focusing the ultrasonic beam radiated therefrom.

20. An ultrasonic transducer for radiating an ultrasonic beam, comprising:

a ceramic substrate having a surface;

a first electrode on the surface of said ceramic substrate, said first electrode radiating a first ultrasonic beam having a beam width which is narrowest at a first distance, said first electrode being diamond-shaped; and a second electrode on the surface of said ceramic substrate, said first and second electrodes combining to radiate a second ultrasonic beam having a beam width which is narrowest at a second distance which is different from the first distance.

21. An ultrasonic transducer as set forth in claim 20, wherein said first and second electrodes are coaxial.

22. An ultrasonic transducer as set forth in claim 21, further comprising an acoustic lens positioned for focusing the first and second ultrasonic beams irradiated from said first and second electrodes.

23. An ultrasonic detection apparatus comprising:

an ultrasonic transducer array comprising a plurality of ultrasonic transducers, each of which includes:

a ceramic substrate having a surface;

a first electrode on the surface of said ceramic substrate, said first electrode radiating a first ultrasonic beam having a beam width which is narrowest at a first distance, said first electrode being dimond-shaped; and a second electrode on the surface of said ceramic substrate, said first and second electrodes combining to radiate a second ultrasonic beam having a beam width which is narrowest at a second distance which is different from the first distance;

an electronic circuit coupled to said transducer array to apply a drive signal to said transducer array and to receive an echo signal from said transducer array; and a display coupled to said electronic circuit to display the echo signal.

* * * * *